United States Patent
Witowski

(10) Patent No.: US 6,497,684 B2
(45) Date of Patent: Dec. 24, 2002

(54) SYRINGE WITH A BARREL HAVING A SEALING CAP TO HOLD A FLUID MEDIUM WITHIN THE BARREL

(75) Inventor: Norbert Witowski, Wolfenbuttel (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/828,234

(22) Filed: Apr. 9, 2001

(65) Prior Publication Data

US 2002/0038104 A1 Mar. 28, 2002

(30) Foreign Application Priority Data

Sep. 27, 2000 (EP) .......................................... 00 121060

(51) Int. Cl.[7] .................................................. A61M 5/32
(52) U.S. Cl. ...................... 604/199; 604/192; 604/238
(58) Field of Search .............................. 604/192, 197, 604/198, 199, 162, 164.08, 263

(56) References Cited

U.S. PATENT DOCUMENTS

| | | | |
|---|---|---|---|
| 2,922,419 A | | 1/1960 | Bednarz |
| 3,916,894 A | | 11/1975 | Cloyd |
| 3,941,128 A | * | 3/1976 | Baldwin .................... 604/199 |
| 4,568,336 A | | 2/1986 | Cooper |
| 4,944,659 A | | 7/1990 | Labbe et al. |
| 4,986,820 A | | 1/1991 | Fischer |
| 5,069,670 A | | 12/1991 | Vetter et al. |
| 5,383,858 A | | 1/1995 | Reilly et al. |
| 5,393,101 A | * | 2/1995 | Matkovich ................... 285/3 |
| 5,397,313 A | | 3/1995 | Gross |
| 5,411,488 A | | 5/1995 | Pagay et al. |
| 5,411,489 A | | 5/1995 | Pagay et al. |
| 5,413,563 A | | 5/1995 | Basile et al. |
| 5,496,285 A | | 3/1996 | Schumacher et al. |
| 5,611,786 A | | 3/1997 | Kirchhofer |
| 5,620,423 A | | 4/1997 | Eykmann et al. |
| 5,624,405 A | * | 4/1997 | Futagawa et al. ........... 604/187 |
| 5,735,825 A | | 4/1998 | Stevens et al. |
| 5,741,232 A | | 4/1998 | Reilly et al. |
| 5,782,815 A | | 7/1998 | Yanai |
| 5,795,333 A | | 8/1998 | Reilly et al. |
| 5,807,345 A | * | 9/1998 | Grabenkort ................. 215/211 |
| 5,997,502 A | | 12/1999 | Reilly et al. |
| 6,053,895 A | | 4/2000 | Kolberg et al. |
| 6,090,064 A | | 7/2000 | Reilly et al. |

FOREIGN PATENT DOCUMENTS

| | | |
|---|---|---|
| AT | 68979 B | 6/1992 |
| DE | 854617 | 7/1949 |
| DE | 2514412 A1 | 10/1976 |
| DE | 2720125 A1 | 11/1978 |
| DE | 3325622 C2 | 1/1986 |
| DE | 4339528 C2 | 9/1995 |
| DE | 19644622 A1 | 4/1998 |

(List continued on next page.)

OTHER PUBLICATIONS

Derwent English Abstract of DE 2514412 A.
Derwent English Abstract of DE 3325622 A.
Derwent English Abstract of DE 2720125 A.

Primary Examiner—Lesley D. Morris
Assistant Examiner—John Fristoe
(74) Attorney, Agent, or Firm—Millen, White, Zelano & Branigan, P.C.

(57) ABSTRACT

A syringe with a barrel for holding a fluid medium includes a sealing cap that is put on the outlet end of the barrel. The barrel in the section that can be inserted into the cap has a first locking element on the outside. The sealing cap in the corresponding section has interactive second locking elements on the inside. The sealing cap can thus be put onto barrel with little force and thus less cracking occurs. To facilitate locking, the cap has a large number of second locking elements that are arranged peripherally. In each case, an expansion section is provided in the wall of cap between each pair of adjacent locking elements.

16 Claims, 1 Drawing Sheet

FOREIGN PATENT DOCUMENTS

| | | |
|---|---|---|
| EP | 397977 A2 | 11/1990 |
| EP | 584531 A2 | 3/1994 |
| EP | 685237 | 12/1995 |
| EP | 0723784 | 7/1996 |
| WO | 8500524 A1 | 2/1985 |
| WO | 8805315 | 7/1988 |
| WO | WO 6501812 | 1/1995 |
| WO | 9530444 A1 | 11/1995 |

* cited by examiner

SYRINGE WITH A BARREL HAVING A SEALING CAP TO HOLD A FLUID MEDIUM WITHIN THE BARREL

FIELD OF THE INVENTION

The invention relates to a syringe with a Barrel having a Sealing Cap to a Fluid Medium within the Barrel.

BACKGROUND OF THE INVENTION

Such a syringe is known from EP 0 723 784 A, incorporated in its entirety by reference. The barrel has a lug that extends in the peripheral direction with an inclined side facing the outlet and a rear shoulder that is almost perpendicular to the peripheral direction. On its inside, the cap that is to be put on has sections that are formed as undercuts and that extend in the peripheral direction, and the cap engages in the projecting section of the barrel when the cap is pushed on. Since the outside diameter of the projecting section of the barrel is larger than the inside diameter of the cap, a considerable compressive force can be used when the cap is put on. This is all the more true as the projecting element must be relatively large so that deviations from the container dimensions can be compensated for.

SUMMARY OF THE INVENTION

The object of the invention is to provide an improved syringe of the type mentioned above.

It is achieved by this design that the compressive pressure can be lower to put on the sealing cap, which in turn has the result that the number of cases in which the container is damaged during closing is reduced.

BRIEF DESCRIPTION OF THE DRAWINGS

Other features and the suitability of the invention follow from the description of the embodiments based on the figures. Here, the figures show:

FIG. 1 shows the outlet-side end of a barrel 1, on which a sealing cap 2 is put for outlet-side sealing. In a known way, barrel 1 has a seal on its inlet side and a sealable plunger in the inside to extrude the medium that is to be held in the barrel. Barrel 1 is designed as a glass barrel, and sealing cap 2 is preferably made of a chlorobutyl rubber or another elastic material having similar properties.

DETAILED DESCRIPTION OF THE INVENTION

Figure 1:
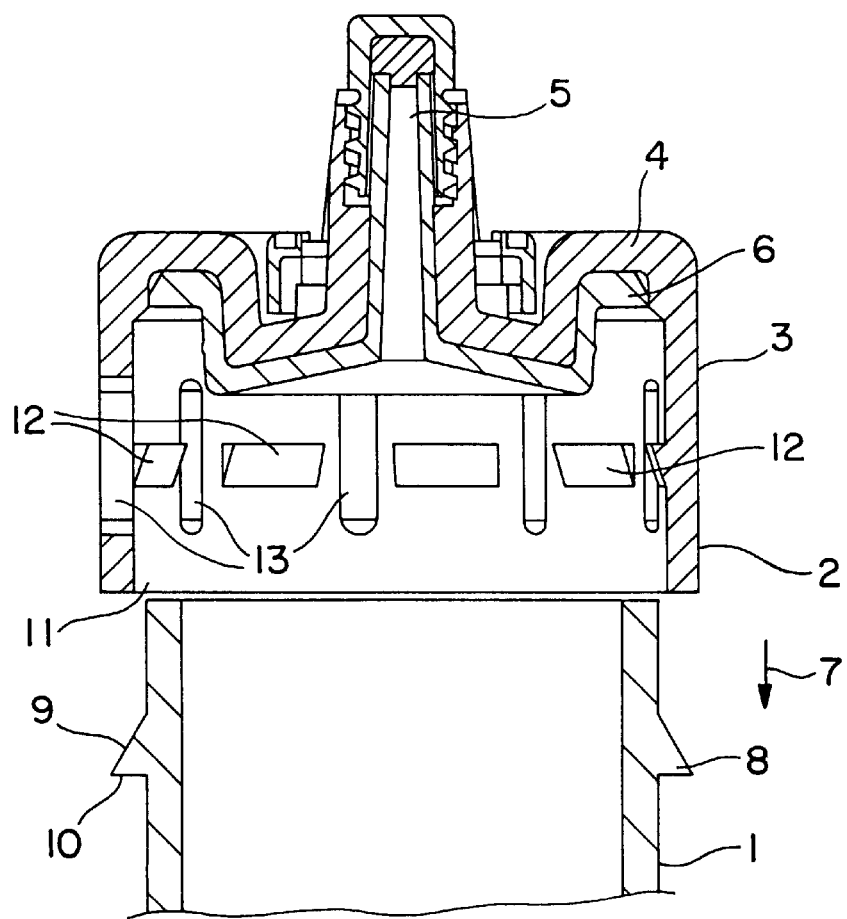
FIG. 1 a section through the outlet-side end of a barrel and through the sealing cap that is to be put on, and FIG. 2 a second embodiment of the outlet-side end of the barrel.

Sealing cap 2 is designed cup-shaped and has a cylindrical wall section 3, which is open to the end facing the barrel and has a cover 4 on the opposite end, whereby the cover has a sealable outlet 5 in a known way. Inside of the cover, a seal 6 is provided. Sealing cap 2 is pushed open to seal the syringe body in the direction of arrow 7 on the outlet-side end of barrel 1.

At a predetermined distance from its outlet-side end, barrel 1 has a first locking element 8 that projects from and extends around the entire periphery thereof. The locking element 8 and which has a cross-section of a sawtooth shape and is tilted like a ramp on its shoulder 9 that faces the outlet-side end, while second shoulder 10 that faces away from the outlet-side end, extends almost perpendicularly to the barrel surface. In other words, the projection has a first surface that converges toward the barrel in the direction of the barrel opening to form a ramp and a second surface 10 that extends transverse to the axis of the barrel 1 to form an abrupt shoulder.

At a predetermined distance from open end 11 of the cap 2, a large number of second locking elements 12 that are placed against one another in peripheral direction are provided on the inside wall. The cross-sections of said locking elements are also designed in an approximately sawtooth shape and have a shoulder that is in turn inclined on its side that faces open end 11 and a shoulder that runs almost perpendicular to the wall of the wall section on its side that faces away from open end 11. The second shoulders lie in a plane that runs perpendicular to the axis of symmetry of the sealing cap. The distance of this plane from open end 11 or from the base of seal 6 is selected in such a way that the sealing cap can be pushed on just to the outlet-side end of barrel 1 so that when the free edge of the barrel adjoins seal 6, second locking elements 12 are slid over first locking element 8, and the two elements make contact and lock with their almost perpendicular shoulders.

As FIG. 1 shows, a longitudinal slot 13 that extends parallel to the axis of symmetry in the wall of the sealing cap is provided between, in each case, two adjacent second locking elements 12. The sealing cap is arranged symmetrically between, in each case, two adjacent locking elements and extends both upward to the sealed bottom of the sealing cap and also downward to open end 11 over the length of locking elements 12.

At least six second locking elements are preferably provided placed against one another in peripheral direction. An embodiment with a number from eight to ten and corresponding longitudinal slots 13 arranged in between in each case is quite especially advantageous.

Figure 2:
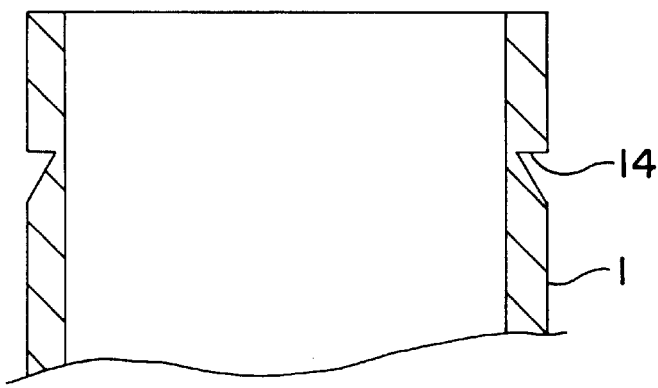

The embodiment that is shown in FIG. 2 is distinguished from the one first described only in that instead of first locking element 8, an annular undercut 14 is provided, which is designed in such. a way that second locking elements 12 project inwardly to engage in the undercut to ensure locking when sealing cap 2 is pushed on.

Longitudinal slots 13 are used as expansion sections and facilitate pushing the sealing cap onto the end of the barrel. The above-discussed number of second locking elements 12 that are arranged according to peripheral direction also contributes to the fact that together with the longitudinal slots, a pushing with less pressure is possible.

In the above-described embodiment, the expansion sections that are formed by longitudinal slots 13 are designed as recesses that extend through the entire wall. As an alternative, it can also be provided that the expansion strips are made only as recesses that do not go through the entire wall. In both cases, the axial length and the width of the expansion strips is selected based on the material that forms the sealing cap and its elasticity properties. In this case, the barrel itself is preferably made of glass.

The requirements for the materials of glass plunger, inlet-side seal, outlet-side sealing cap and plunger, which together form a glass cartridge, are high, since they are sterilized both in unassembled state and as assembled syringes at about 120° C. over an extended period of, for example, 30 minutes with superheated water.

The entire disclosure of all applications, patents and publications, cited above and below, and of corresponding European Application No. 00121060.8, filed Sep. 27, 2000 is hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A syringe comprising:

a barrel (1) for holding a fluid medium and having a sealing cap (2) that is placed on the outlet side thereof, wherein the barrel (1) has a section that can be inserted into the cap (2) and has a first locking element (8) on the outside surface thereof with the cap (2) in a corresponding section having interactive second locking elements (12) on the inside surface thereof; wherein the cap (2) has a plurality of second locking elements (12) that are arranged around its periphery and has expansion sections (13) provided between adjacent locking elements (12) in the wall of cap (2), and wherein the number of second locking elements (12) is at least six, which locking elements are dispersed around the periphery of the cap (2) and between which locking elements the expansion sections are positioned.

2. A syringe according to claim 1, wherein the expansion sections (13) extend axially with respect to the cap (2).

3. A syringe according to claim 2, wherein each expansion section (13) is designed as an elongated section that extends in axial direction beyond the axial dimensions of second locking elements (12).

4. A syringe according to claim 3, wherein the expansion section (13) is configured as a reduced wall section.

5. A syringe according to claim 3, wherein the expansion section is designed as a recess.

6. A syringe according to claim 5, wherein the first locking element (8) is configured as a lug that projects around the barrel outer surface, the first locking element (8) having a section (9) that faces the outlet end of the barrel and is inclined and having a shoulder (10) that extends transverse to-the barrel and faces away from the outlet.

7. A syringe according to claim 5, wherein first locking element (8) is designed a peripheral notch (14) that extends around the barrel.

8. A syringe according to claim 1, wherein the expansion section (13) is configured as a reduced wall section.

9. A syringe according to claim 1, wherein each expansion section (13) is designed as a recess.

10. A syringe according to claim 1, wherein the first locking element (8) is configured as a lug that projects around the barrel outer surface, the first locking element (8) having a section (9) that faces the outlet end of the barrel and is inclined and having a shoulder (10) that extends transverse to the barrel and faces away from the outlet.

11. A syringe according to claim 1, wherein first locking element (8) is designed a peripheral notch (14) that extends around the barrel.

12. A syringe according to claim 1 wherein the cap (2) is made of chlorobutye rubber.

13. A syringe comprising:

a barrel (1) for holding a fluid medium and having a sealing cap (2) that is placed on the outlet side thereof, wherein the barrel (1) has a section that can be inserted into the cap (2) and has a first locking element (8), configured as a peripheral notch 14 in the outside surface thereof, with the cap (2) in a corresponding section having interactive second locking elements (12) on the inside surface thereof; wherein the cap (2) has a plurality of second locking elements (12) that are arranged around its periphery and has expansion sections (13) configured as recesses which extend axially beyond the axial dimension of the second locking elements (12), the expansion sections being provided between adjacent locking elements (12) in the wall of cap (2), and wherein the number of second locking elements (12) is at least six, which locking elements are dispersed around the periphery of the cap (2) and between which locking elements the expansion sections are positioned.

14. A syringe according to claim 13 wherein the cap (2) is made of chlorobutye rubber.

15. A syringe according to claim 13, wherein the first locking element (8) is configured as a lug that projects around the barrel outer surface, the first locking element (8) having a section (9) that faces the outlet end of the barrel and is inclined, the first locking element having a shoulder (10) that extends transverse to the barrel and faces away from the outlet.

16. A syringe according to claim 13, wherein first locking element (8) is designed a peripheral notch (14) that extends around the barrel.

* * * * *

UNITED STATES PATENT AND TRADEMARK OFFICE
CERTIFICATE OF CORRECTION

PATENT NO. : 6,497,684 B2
DATED : December 24, 2004
INVENTOR(S) : Witowski

It is certified that error appears in the above-identified patent and that said Letters Patent is hereby corrected as shown below:

Title page,
Item [30], change "00 121060" to -- 00 121060.8 --.

Column 3,
Line 38, change "to-the" to -- to the --.

Column 4,
Line 11, change "chlorobutye" to -- chlorobutyl --.
Line 17, change "14" to -- (14) --.
Line 33, change "chlorobutye" to -- chlorobutyl --.

Signed and Sealed this

Twelfth Day of October, 2004

JON W. DUDAS
*Director of the United States Patent and Trademark Office*